United States Patent
Park et al.

(10) Patent No.: US 9,031,629 B2
(45) Date of Patent: May 12, 2015

(54) NON-CONTACT PHOTOPLETHYSMOGRAPHIC PULSE MEASUREMENT DEVICE AND OXYGEN SATURATION AND BLOOD PRESSURE MEASUREMENT DEVICES USING THE SAME

(75) Inventors: Kwang Suk Park, Seoul (KR); Hyun Jae Baek, Chungbuk (KR)

(73) Assignee: SNU R&DB Foundation, Seoul (KR)

( * ) Notice: Subject to any disclaimer, the term of this patent is extended or adjusted under 35 U.S.C. 154(b) by 1337 days.

(21) Appl. No.: 12/408,295

(22) Filed: Mar. 20, 2009

(65) Prior Publication Data

US 2010/0185068 A1   Jul. 22, 2010

(30) Foreign Application Priority Data

Jan. 21, 2009   (KR) .................. 10-2009-0005142

(51) Int. Cl.
*A61B 5/1455* (2006.01)
*A61B 5/024* (2006.01)
*A61B 5/021* (2006.01)
(Continued)

(52) U.S. Cl.
CPC .............. *A61B 5/02433* (2013.01); *A61B 5/021* (2013.01); *A61B 5/02438* (2013.01); *A61B 5/0255* (2013.01); *A61B 5/0402* (2013.01); *A61B 5/14551* (2013.01)

(58) Field of Classification Search
CPC ............... A61B 5/021; A61B 5/02433; A61B 5/14551; A61B 5/0255; A61B 5/02438; A61B 5/0402

USPC ......... 600/485, 490, 336, 544, 310, 324, 301, 600/508, 513; 367/7
See application file for complete search history.

(56) References Cited

U.S. PATENT DOCUMENTS

| | | | |
|---|---|---|---|
| 5,857,975 A * | 1/1999 | Golub | 600/485 |
| 6,278,889 B1 * | 8/2001 | Robinson | 600/322 |
| 6,801,799 B2 * | 10/2004 | Mendelson | 600/330 |

(Continued)

OTHER PUBLICATIONS

Kim et al., "A new approach for non-intrusive monitoring of blood pressure on a toilet seat," *Physiol. Meas.* (2006) 27: 203-211.

(Continued)

*Primary Examiner* — Sean Dougherty
*Assistant Examiner* — Michael C Stout
(74) *Attorney, Agent, or Firm* — H.C. Park & Associates, PLC

(57) ABSTRACT

The present invention provides a non-contact photoplethysmographic (PPG) pulse measurement device, and oxygen saturation and blood pressure measurement devices using the PPG pulse measurement device. The PPG pulse measurement device includes a sensing unit including at least two light emitting units for emitting light into a human body without making direct contact with skin, and a light receiving unit for sensing reflected light. A signal separation unit separates output of the sensing unit into a ripple component and a ripple-free component. A microprocessor unit monitors the ripple-free component and compares the ripple-free component with a DC signal value. A luminance adjustment unit adjusts luminance of the light emitting units. A filter and amplification unit eliminates noise from the ripple component. An A/D conversion unit converts output of the filter and amplification unit into a digital signal. A signal transmission unit transmits output of the A/D conversion unit.

16 Claims, 14 Drawing Sheets

(51) Int. Cl.
*A61B 5/0255* (2006.01)
*A61B 5/0402* (2006.01)

(56) References Cited

U.S. PATENT DOCUMENTS

| | | | | |
|---|---|---|---|---|
| 7,215,987 | B1 * | 5/2007 | Sterling et al. | 600/336 |
| 7,291,112 | B2 * | 11/2007 | Martin et al. | 600/485 |
| 7,367,949 | B2 * | 5/2008 | Korhonen et al. | 600/483 |
| 7,729,732 | B2 * | 6/2010 | Ohashi | 600/310 |
| 2003/0144584 | A1 * | 7/2003 | Mendelson | 600/323 |
| 2003/0163033 | A1 * | 8/2003 | Dekker | 600/323 |
| 2004/0116969 | A1 * | 6/2004 | Owen et al. | 607/6 |
| 2004/0260161 | A1 * | 12/2004 | Melker et al. | 600/340 |
| 2007/0106136 | A1 * | 5/2007 | Sterling et al. | 600/336 |
| 2007/0293746 | A1 * | 12/2007 | Sarussi et al. | 600/330 |
| 2008/0167541 | A1 * | 7/2008 | Takala et al. | 600/323 |
| 2009/0131774 | A1 * | 5/2009 | Sweitzer et al. | 600/323 |
| 2009/0182208 | A1 * | 7/2009 | Cho et al. | 600/310 |
| 2009/0259116 | A1 * | 10/2009 | Wasserman et al. | 600/323 |
| 2009/0281402 | A1 * | 11/2009 | Chance | 600/328 |
| 2009/0306487 | A1 * | 12/2009 | Crowe et al. | 600/322 |
| 2011/0043225 | A1 * | 2/2011 | Sullivan et al. | 324/658 |

OTHER PUBLICATIONS

Chen et al., "Continuous estimation of systolic blood pressure using the pulse arrival time and intermittent calibration," *Med. Biol. Eng. Comput.* (2000) 38: 569-574.

Lim et al., "ECG measurement on a chair without conductive contact," *IEEE Transactions on Biomedical Engineering* (2006) 53 (5): 956-959.

Geddes et al., "Pulse transit time as an indicator of arterial blood pressure," *Psychophysiology* (1981) 18 (1): 71-74.

* cited by examiner

NON-CONTACT PHOTOPLETHYSMOGRAPHIC PULSE MEASUREMENT DEVICE AND OXYGEN SATURATION AND BLOOD PRESSURE MEASUREMENT DEVICES USING THE SAME

CROSS REFERENCE TO RELATED APPLICATION(S)

This application claims the benefit of Korean Patent Application No. 10-2009-0005142, filed on Jan. 21, 2009, entitled "Non-Contact Measuring Devices of Pulse Wave and Measuring Devices of Oxygen Saturation and Blood Pressure In Using Same," which is hereby incorporated by reference in its entirety into this application. A claim of priority to this application, to the extent appropriate, is made.

BACKGROUND OF THE INVENTION

1. Field of the Invention

The present invention relates, in general, to a non-contact photoplethysmographic pulse measurement device, and oxygen saturation and blood pressure measurement devices using the non-contact photoplethysmographic pulse measurement device, and, more particularly, to a non-contact photoplethysmographic pulse measurement device, and oxygen saturation and blood pressure measurement devices using the non-contact photoplethysmographic pulse measurement device, which can measure a photoplethysmographic pulse, oxygen saturation and an electrocardiogram without making direct contact with a user's skin while the user is unaware of the measurement being taken, and can measure blood pressure using both the photoplethysmographic pulse and the electrocardiogram.

2. Description of the Related Art

Whenever the heart is contracted, blood is supplied from the heart to the whole body through the main artery, and, at this time, variation in pressure occurs in the main artery. Such variation in pressure is transferred up to the peripheral arterioles of the hands and feet. The term 'photoplethysmographic (PPG) pulse' means a pulse wave representing variation in the volume of peripheral blood vessels, attributable to variation in the internal pressure of the artery.

The volume of a blood vessel changes due to such a pulsation. When light having a certain wavelength such as infrared light or visible light is provided to a blood vessel, the volume of the blood vessel increases or decreases, and thus the amount of light absorbed by the blood vessel changes. For example, when light of 100 is emitted, the amount of light which is reflected and is not absorbed may change following the beat of the pulse.

On the basis of this principle, after light is emitted through a light emitting unit, the speed or amount of reflected infrared light is input to a light receiving unit, and then a photoplethysmographic (PPG) pulse can be measured using the characteristic that current and voltage vary according to the speed or amount of input infrared light.

A conventional PPG pulse measurement device performs measurement by bringing a sensing unit into contact with the skin so as to measure a PPG pulse. Accordingly, there is a disadvantage in that the skin must always be maintained in a clean state, and an examinee must assume a peaceful attitude so that his or her mental state does not influence the waveform of the pulse wave.

In order to overcome this disadvantage, a non-contact PPG pulse measurement device, which is capable of measuring a PPG pulse through the clothing of a user without making direct contact with the skin while the user is unaware of the measurement being taken, is required.

To measure a PPG pulse through clothing, light, which is emitted from a light emitting unit, must be able to pass through the clothing and enter the skin tissue and the artery, and light, which is not absorbed and is reflected, must pass through the clothing and reach a light receiving unit. For this operation, it is necessary to emit light with a higher luminance than that of light used at the time of measuring a PPG pulse on the skin such as is used in the case of the conventional technology.

As shown in FIGS. 9A to 9B, the sensing unit of a conventional PPG pulse measurement device is configured such that one light emitting unit 10, implemented using a Light Emitting Diode (LED), and one light receiving unit 20, implemented using a photodetector, are arranged in parallel with each other. Meanwhile, since the LED radiates light in a circular pattern, only part of the light reflected from the tissue of a human body is incident on a sensing area of the light receiving unit 20. That is, there is a problem in that, of a total amount of reflected light, a large amount of that light is not sensed by the light receiving unit 20. Therefore, the revision of the sensing unit is required to emit high-luminance light.

Meanwhile, since light emitted with high luminance causes the saturation of signals, a PPG pulse measurement device capable of emitting light having suitable luminance according to the thickness of clothing is required.

SUMMARY OF THE INVENTION

Accordingly, the present invention has been made keeping in mind the above problems occurring in the prior art, and an object of the present invention is to provide a non-contact photoplethysmographic (PPG) pulse measurement device, and oxygen saturation and blood pressure measurement devices using the PPG pulse measurement device, which can measure the PPG pulse, oxygen saturation and blood pressure of a user in the state in which the user is wearing his or her clothes without making direct contact with the skin while the user is unaware of the measurement being taken.

Another object of the present invention is to provide a device, which can measure the PPG pulse of a user using a tool, such as a chair or a bed, encountered normally in the course of the user's daily life regardless of a difference in the thickness of clothing, and can also measure the oxygen saturation of the user in an unconstrained manner.

A further object of the present invention is to provide a device, which measures a pulse arrival time in conjunction with an electrocardiogram measurement system capable of performing measurement through clothing, thus enabling blood pressure to be continuously estimated.

In order to accomplish the above objects, the present invention provides a non-contact photoplethysmographic (PPG) pulse measurement device, comprising a sensing unit including at least two light emitting units for emitting light into a human body without making direct contact with skin of a user, and a light receiving unit arranged around the light emitting units and configured to sense light reflected from the human body, a signal separation unit implemented as a filter for separating an output of the sensing unit into a ripple component and a ripple-free component, a microprocessor unit configured to monitor the ripple-free component, compare a value of the ripple-free component with a preset Direct Current (DC) signal value, and generate a control signal commanding luminance to be increased when the value of the ripple-free component is less than the DC signal value, a luminance adjustment unit configured to adjust luminance of the light emitting units in response to the control signal output from the microprocessor unit, a filter and amplification unit including a filter for eliminating noise from the ripple component and an amplifier for amplifying a filtered ripple component, an Analog/Digital (A/D) conversion unit configured to convert an output of the filter and amplification unit into a digital signal, and a signal transmission unit configured to transmit an output of the A/D conversion unit to an external device.

Preferably, the light emitting units may be arranged on a circumference of a circle having a predetermined radius and the light receiving unit may be arranged at a center of the circle.

Preferably, the light emitting units include three light emitting units, which are arranged and spaced apart from each other at equal 120° intervals around the light receiving unit.

Preferably, the DC signal value preset in the microprocessor unit may be 1V to 2V.

Further, the present invention provides a non-contact photoplethysmographic (PPG) pulse measurement device, comprising a sensing unit including a light emitting unit for emitting light into a human body without making direct contact with skin, and at least two light receiving units arranged around the light emitting unit and configured to sense light reflected from the human body, a signal separation unit implemented as a filter for separating an output of the sensing unit into a ripple component and a ripple-free component, a microprocessor unit configured to monitor the ripple-free component, compare a value of the ripple-free component with a preset Direct Current (DC) signal value, and generate a control signal commanding luminance to be increased when the value of the ripple-free component is less than the DC signal value, a luminance adjustment unit configured to adjust luminance of the light emitting units in response to the control signal output from the microprocessor unit, a filter and amplification unit including a filter for eliminating noise from the ripple component and an amplifier for amplifying a filtered ripple component, an Analog/Digital (A/D) conversion unit configured to convert an output of the filter and amplification unit into a digital signal, and a signal transmission unit configured to transmit an output of the A/D conversion unit to an external device.

Preferably, the light emitting unit may be arranged at a center of a circle having a predetermined radius, and the light receiving units may be arranged on a circumference of the circle.

Preferably, the light receiving units may include three light receiving units, which are arranged and spaced apart from each other at equal 120° intervals around the light emitting unit. In this case, the DC signal value preset in the microprocessor unit may be 1V to 2V.

Further, the present invention provides a non-contact oxygen saturation measurement device, comprising a sensing unit including at least four light emitting units for emitting light having different wavelengths into a human body without making direct contact with skin, and a light receiving unit arranged around the light emitting units and configured to sense light reflected from the human body, wherein a number of light emitting units that emit light having each wavelength is uniform, a signal separation unit configured to classify an output of the sensing unit into respective wavelengths and separate the output into a ripple component and a ripple-free component for each wavelength, a microprocessor unit configured to monitor the ripple-free component, compare a value of the ripple-free component with a preset Direct Current (DC) signal value, and generate a control signal commanding luminance to be increased when the value of the ripple-free component is less than the DC signal value, a luminance adjustment unit configured to adjust luminance of the light emitting units in response to the control signal output from the microprocessor unit, a filter and amplification unit including a filter for eliminating noise from the ripple component and an amplifier for amplifying a filtered ripple component, an Analog/Digital (A/D) conversion unit configured to convert an output of the filter and amplification unit into a digital signal, and a signal transmission unit configured to transmit an output of the A/D conversion unit to an external device.

Preferably, the light emitting units may be arranged on a circumference of a circle having a predetermined radius and the light receiving unit may be arranged at a center of the circle, wherein three light emitting units for emitting red light are included in the light emitting units to correspond to three light emitting units for emitting infrared light.

Preferably, the light emitting units may be configured such that the light emitting units for emitting the infrared light and the light emitting units for emitting the red light are sequentially and alternately arranged so that they are arranged and spaced apart from each other at equal 60° intervals around the light receiving unit.

Further, the present invention provides a non-contact oxygen saturation measurement device, comprising a sensing unit including at least two light emitting units for emitting light having different wavelengths into a human body without making direct contact with skin and at least two light receiving units arranged around the light emitting units and configured to sense light reflected from the human body, wherein a number of light emitting units that emit light having each wavelength is uniform, a signal separation unit configured to classify an output of the sensing unit into respective wavelengths and separate the output into a ripple component and a ripple-free component for each wavelength, a microprocessor unit configured to monitor the ripple-free component, compare a value of the ripple-free component with a preset Direct Current (DC) signal value, and generate a control signal commanding luminance to be increased when the value of the ripple-free component is less than the DC signal value, a luminance adjustment unit configured to adjust luminance of the light emitting units in response to the control signal output from the microprocessor unit, a filter and amplification unit including a filter for eliminating noise from the ripple component and an amplifier for amplifying a filtered ripple component, an Analog/Digital (A/D) conversion unit configured to convert an output of the filter and amplification unit into a digital signal, and a signal transmission unit configured to transmit an output of the A/D conversion unit to an external device.

Preferably, the light emitting units may be arranged in parallel around a center of a circle having a predetermined radius so that one light emitting unit for emitting red light is included to correspond to one light emitting unit for emitting infrared light, and the light receiving units may be arranged on a circumference of the circle.

Preferably, the light receiving units may include three light receiving units, which are arranged and spaced apart from each other at equal 120° intervals around a center of the circle on which the light receiving units are arranged.

In addition, the present invention provides a non-contact blood pressure measurement device, comprising the non-contact PPG pulse measurement device, a non-contact electrocardiogram measurement device for measuring an electrocardiogram without making direct contact with skin, and a signal processing device for outputting blood pressure information using both a signal transmitted from the non-contact PPG pulse measurement device and a signal transmitted from the non-contact electrocardiogram measurement device.

Preferably, the non-contact electrocardiogram measurement device may comprise an amplifier-attached electrode, a filter and amplification unit including a filter for eliminating noise from a signal output from the amplifier-attached electrode, and an amplifier for amplifying a filtered signal, an A/D conversion unit for converting an output of the filter and amplification unit into a digital signal, and a signal transmission unit for transmitting an output of the A/D conversion unit to the signal processing device.

Preferably, the signal processing device may comprise a pulse arrival time calculation unit for calculating a pulse arrival time using the signals transmitted from the non-contact PPG pulse measurement device and the non-contact electrocardiogram measurement device, a blood pressure information output unit for outputting blood pressure information corresponding to the pulse arrival time calculated by the pulse arrival time calculation unit in conjunction with a blood pressure information database, and a display unit for displaying an output of the blood pressure information output unit on a screen.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
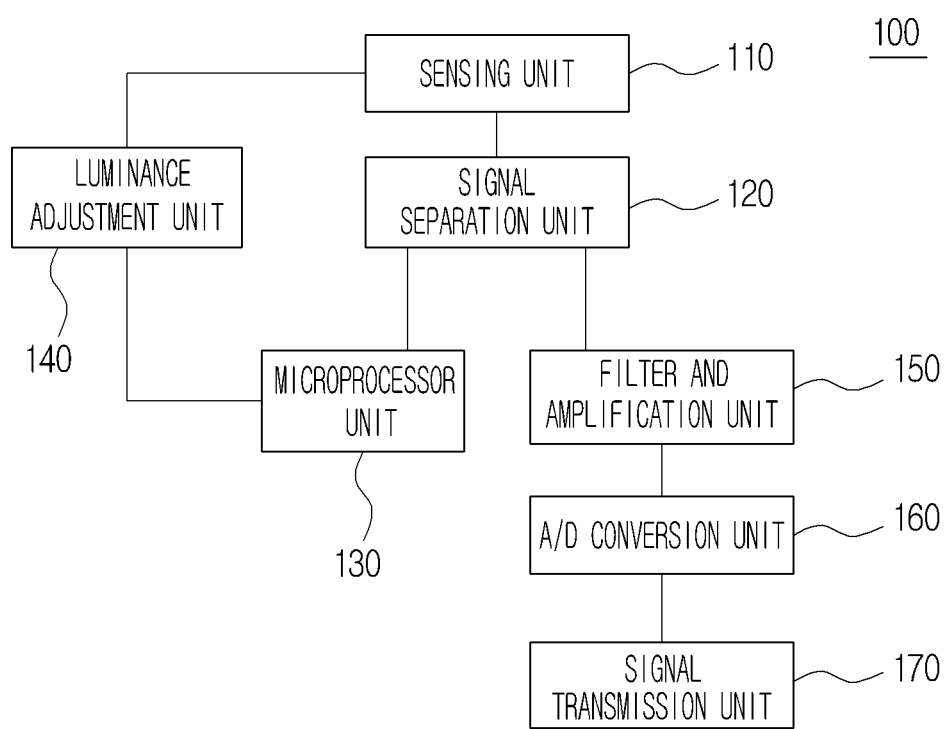
FIG. 1 is a schematic block diagram showing the construction of a non-contact PPG pulse measurement device according to an embodiment of the present invention.

Hereinafter, embodiments of the present invention will be described in detail with reference to the attached drawings. Reference now should be made to the drawings, in which the same reference numerals are used throughout the different drawings to designate the same or similar components. In the description of the present invention, a description of related well-known functions or constructions will be omitted to prevent the gist of the present invention from becoming unclear.

Figure 2A:
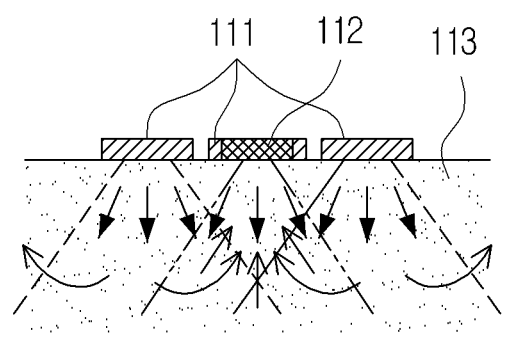
FIG. 2A is a front view showing a first construction of the sensing unit of the non-contact PPG pulse measurement device according to an embodiment of the present invention.
Figure 2B:
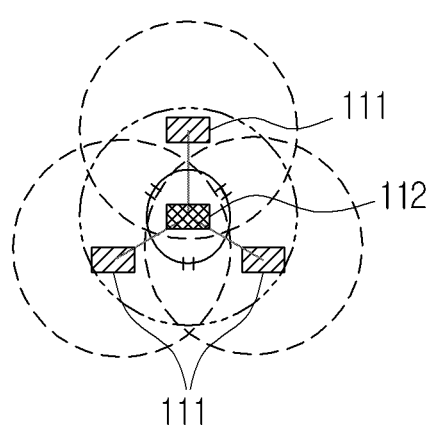
FIG. 2B is a top view showing the first construction of the sensing unit of the non-contact PPG pulse measurement device according to an embodiment of the present invention.
Figure 3A:
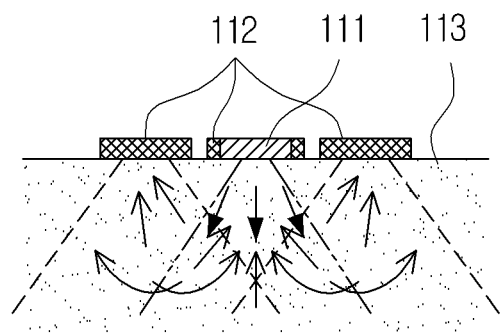
FIG. 3A is a front view showing a second construction of the sensing unit of the non-contact PPG pulse measurement device according to an embodiment of the present invention.
Figure 3B:
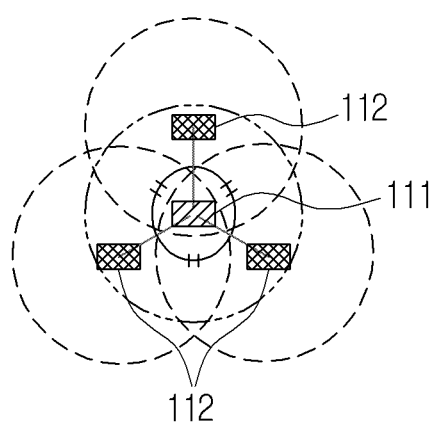
FIG. 3B is a top view showing the second construction of the sensing unit of the non-contact PPG pulse measurement device according to an embodiment of the present invention.
Figure 4A:
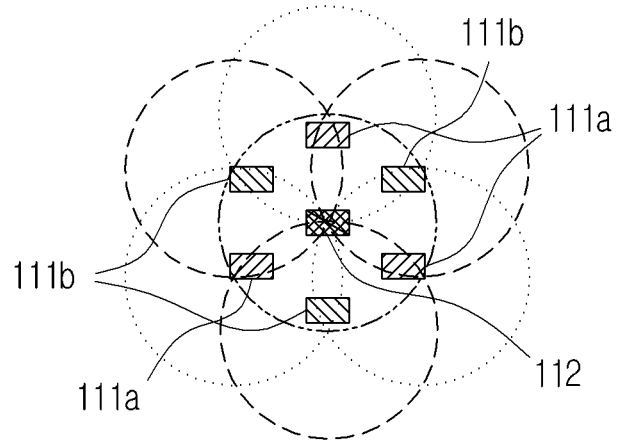
FIG. 4A is a front view showing the construction of the sensing unit of a non-contact oxygen saturation measurement device according to an embodiment of the present invention.
Figure 4B:
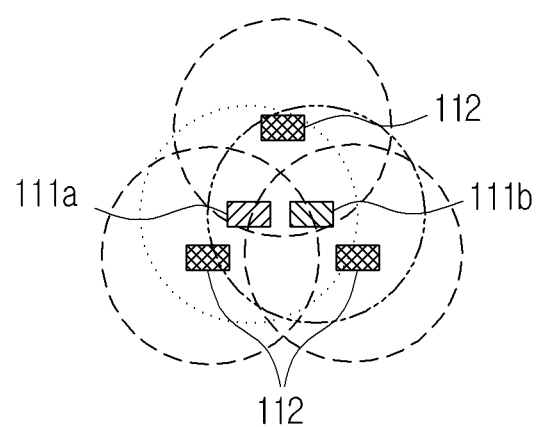
FIG. 4B is a top view showing the construction of the sensing unit of the non-contact oxygen saturation measurement device according to an embodiment of the present invention.
Figure 5:
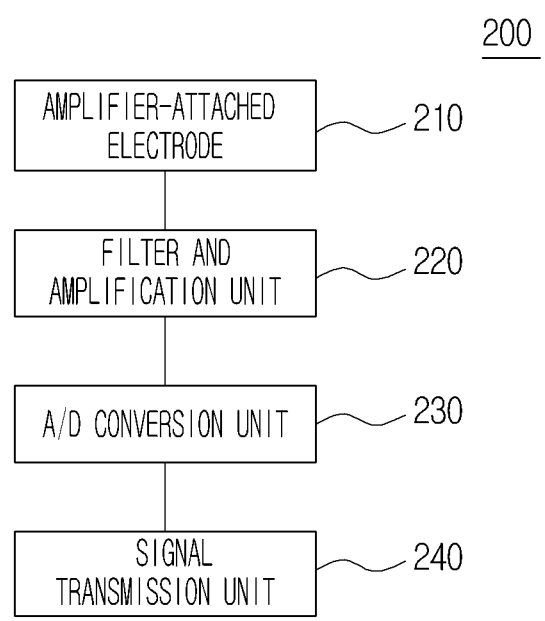
FIG. 5 is a schematic block diagram showing the construction of a non-contact electrocardiogram measurement device according to an embodiment of the present invention.
Figure 6A:
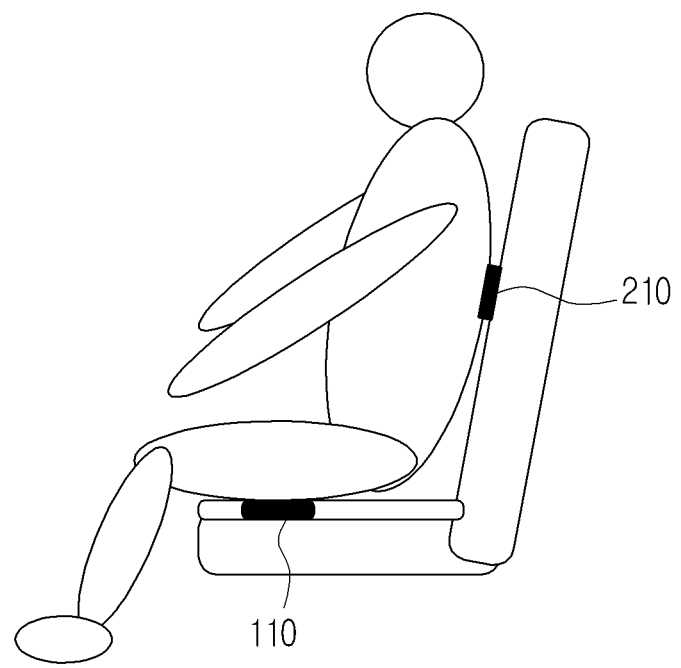
FIGS. 6A and 6B are schematic diagrams showing a structure for measuring a PPG pulse and an electrocardiogram using the non-contact PPG pulse measurement device and the non-contact electrocardiogram measurement device which are applied to a chair according to an embodiment of the present invention.
Figure 6B:
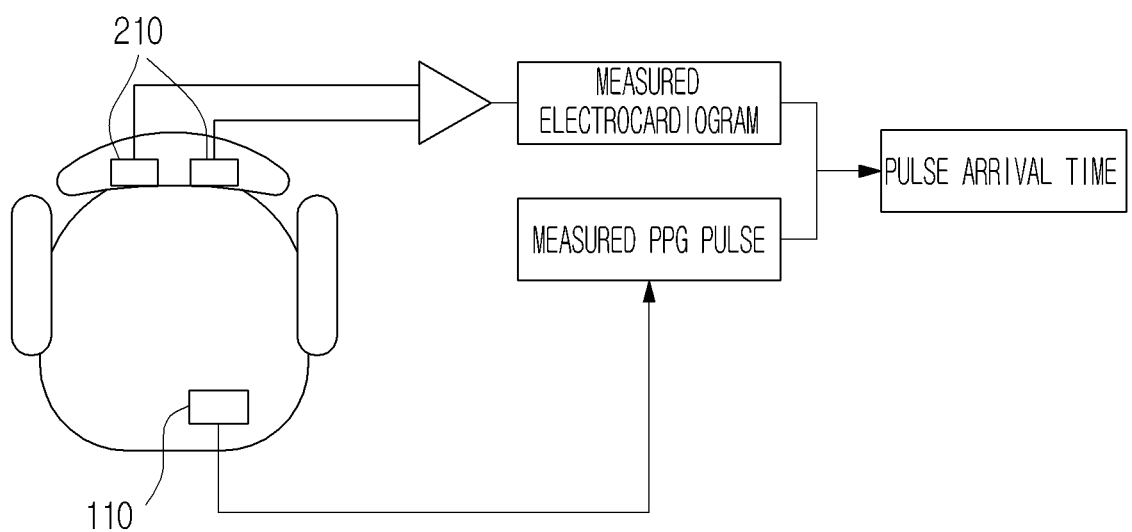
Figure 7:
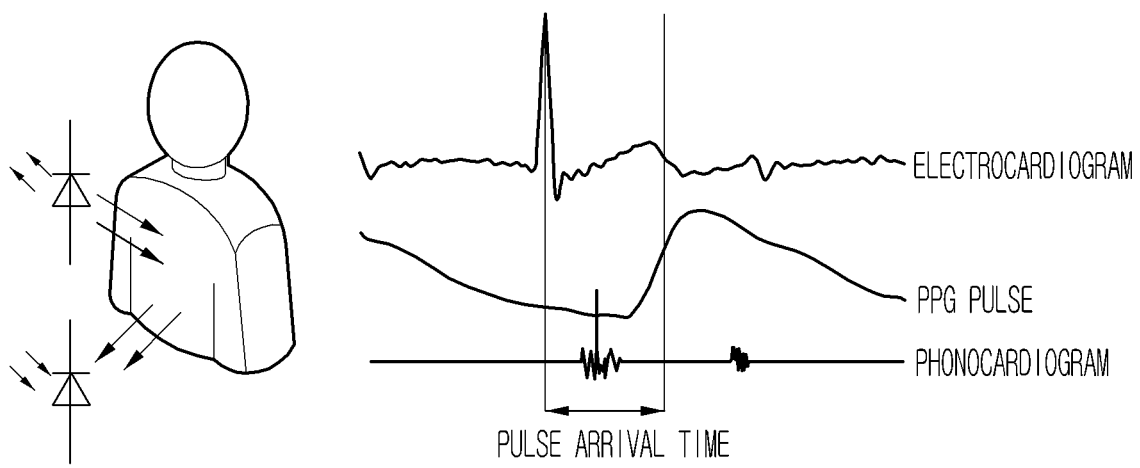
FIG. 7 is a diagram showing the definition of a pulse arrival time.
Figure 8:
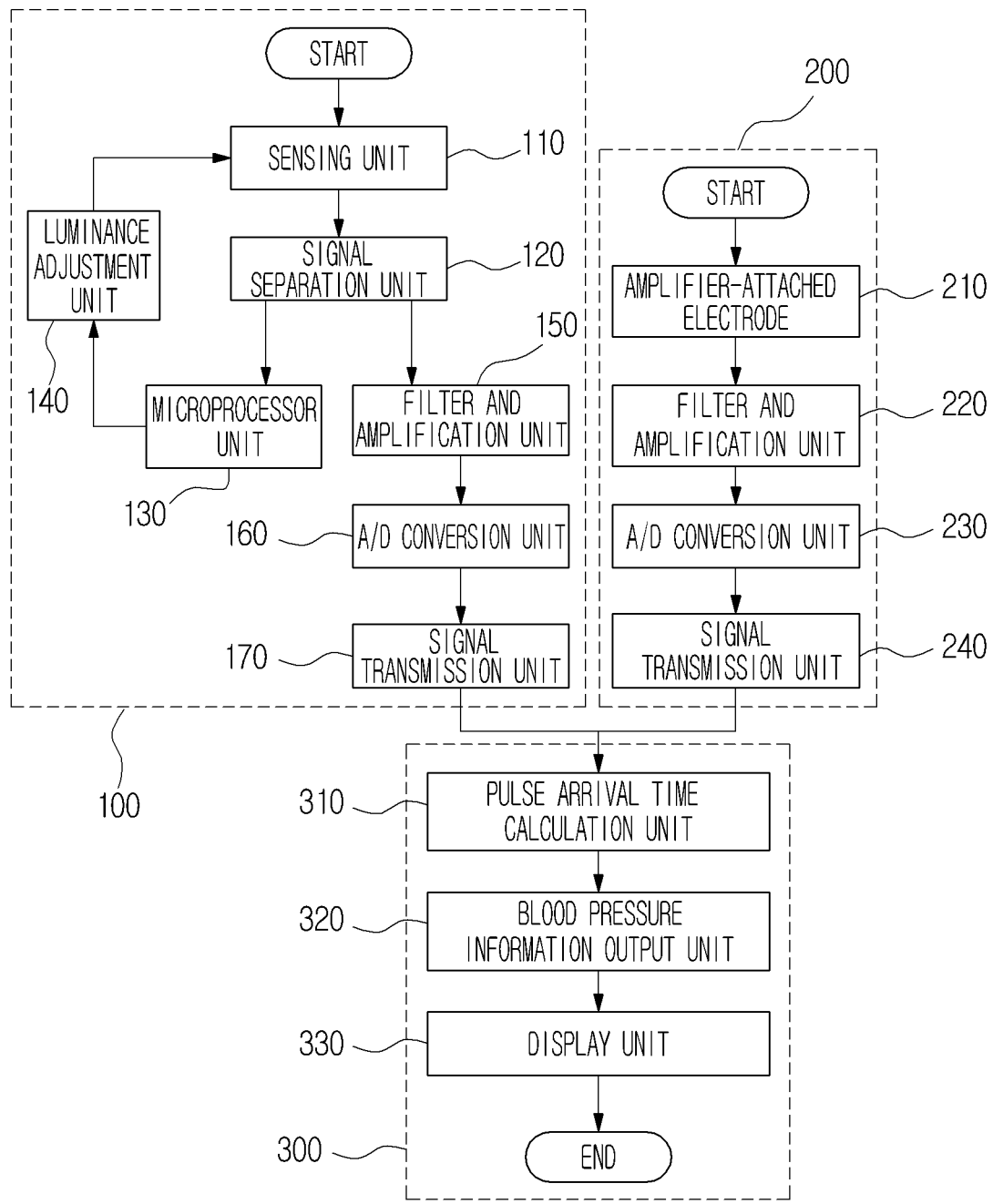
FIG. 8 is a schematic diagram showing a non-contact blood pressure measurement device according to an embodiment of the present invention.
Figure 9A:
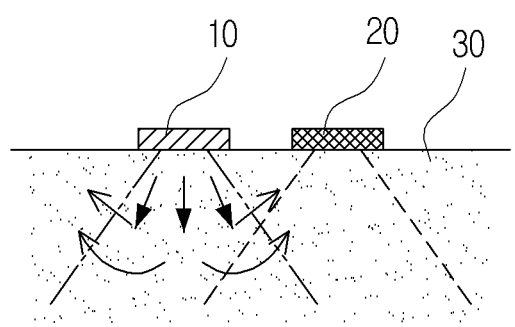
FIG. 9A is a front view showing the construction of the sensing unit of a conventional PPG pulse measurement device.
Figure 9B:
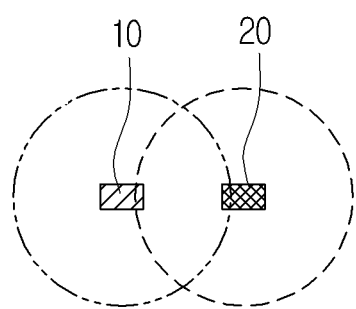
FIG. 9B is a top view showing the construction of the sensing unit of the conventional PPG pulse measurement device.

FIG. 1 is a schematic diagram showing the construction of a non-contact PPG pulse measurement device according to an embodiment of the present invention, FIGS. 2A and 2B are diagrams showing the first construction of the sensing unit of the non-contact PPG pulse measurement device according to an embodiment of the present invention, FIGS. 3A and 3B are diagrams showing the second construction of the sensing unit of the non-contact PPG pulse measurement device, FIGS. 4A and 4B are diagrams showing the construction of the sensing unit of a non-contact oxygen saturation measurement device according to an embodiment of the present invention, FIG. 5 is a schematic diagram showing the construction of a non-contact electrocardiogram measurement device according to an embodiment of the present invention, FIGS. 6A and 6B are schematic diagrams showing a structure for measuring a PPG pulse and an electrocardiogram using the non-contact PPG pulse measurement device according to an embodiment of the present invention applied to a chair, FIG. 7 is a diagram showing the definition of pulse arrival time, FIG. 8 is a schematic block diagram showing a non-contact blood pressure measurement device according to an embodiment of the present invention, and FIGS. 9A and 9B are diagrams showing the construction of the sensing unit of a conventional PPG pulse measurement device.

As shown in FIG. 1, a non-contact photoplethysmographic (PPG) pulse measurement device according to a first embodiment of the present invention includes a sensing unit 110, a signal separation unit 120, a microprocessor unit 130, a luminance adjustment unit 140, a filter and amplification unit 150, an Analog/Digital (A/D) conversion unit 160, and a signal transmission unit 170.

The sensing unit 110 is implemented using reflection-type sensors, and includes at least two light emitting units for emitting light and a light receiving unit for sensing light which has been emitted from the light emitting units and has been reflected from a human body.

The sensing unit 110 measures the PPG pulse of the human body, but measures the PPG pulse in an unconstrained manner without making direct contact with the skin of a user, that is, without the user's awareness of the measurement being taken. For example, the sensing unit 110 comes into contact with the clothing of the user without the user's awareness of the measurement being taken while the user is wearing his or her clothes in his or her daily life, thus enabling the measurement of the PPG pulse of the human body.

The light emitting units are implemented as Light Emitting Diodes (LEDs) which emit infrared light, and the light receiving unit is implemented as a photodetector. In this case, a plurality of light emitting units may be arranged around and near a single light receiving unit. In detail, the light emitting units may be arranged on the circumference of a circle having a predetermined radius, and the light receiving unit may be arranged at the center of the circle.

As an example, the sensing unit may be implemented using two light emitting units so that the light emitting units are arranged to be collinear while being spaced apart from each other by an angle of 180° around the light receiving unit. Further, as another example, as shown in FIGS. 2A and 2B, the sensing unit includes three light emitting units 111 so that the light emitting units 111 are arranged and spaced apart from each other at equal 120° intervals around the light receiving unit 112. At this time, the distance between each light emitting unit 111 and the center of the light receiving unit 112 may be 10 mm.

The sensing unit 110 may be installed at a predetermined location on the top surface of a chair coming into contact with the hips of the user and may measure the PPG pulse of an examinee on a thigh portion of the examinee in an unconstrained manner. Further, the sensing unit 110 may be installed on another piece of furniture closely related to the daily life of the user, such as a bed or a sofa, to measure a PPG pulse. In addition, it is apparent that a PPG pulse can be measured in an unconstrained manner from the carotid artery, the radial artery, the fingertip pulse, the femoral artery, or the dorsalis pedis artery, through clothes worn on an arm or a leg.

The signal separation unit 120 may be implemented as a filter for separating the output of the sensing unit 110 into a ripple component and a ripple-free component.

The ripple component (Alternating Current [AC] component, hereinafter referred to as a 'ripple component') is a pulse signal obtained due to the contraction and relaxation of an arterial blood vessel, and is extracted by a band pass filter. The ripple-free component (Direct Current [DC] component, hereinafter referred to as a 'ripple-free component') is a signal, having a certain magnitude, obtained by another tissue, and is extracted by a low pass filter.

The microprocessor unit 130 monitors the ripple-free component, compares the value of the ripple-free component with a preset DC signal value, and generates a control signal commanding luminance to be increased when the value of the ripple-free component is less than the DC signal value. Of course, in contrast, when the value of the ripple-free component is greater than the DC signal value, the microprocessor unit 130 generates a control signal commanding the luminance to be decreased.

The value of the ripple-free component changes according to an examinee or a measurement location. The principal cause of this change is the thickness of clothing and absorption factors of the components of the clothing. In order to measure a suitable PPG pulse, the value of the ripple-free component must be 1V to 2V. Therefore, the value set in the microprocessor unit 130 may preferably be a 1V to 2V.

The luminance adjustment unit 140 adjusts the luminance of the light emitting units 111 in response to the control signal output from the microprocessor unit 130. The luminance of the light emitting units 111 of the sensing unit 110 required to allow the value of the ripple-free component to be from 1V to 2V differs for respective examinees or their clothing. Therefore, the luminance adjustment unit 140 is implemented such that, when the ripple-free component does not fall within a range of values set in the microprocessor unit 130, the luminance of the light emitting units 111 is suitably changed. Since the LEDs of the light emitting units 111 are driven by voltage, which is output from a Digital/Analog Converter (DAC) in response to digital input received from the microprocessor unit, the adjustment of luminance is possible. Therefore, when the value of the ripple-free component is greater than 2V, the luminance adjustment unit 140 decreases the luminance of the light emitting units 111 in response to the control signal output from the microprocessor unit 130, whereas, when the value of the ripple-free component is less than 1V, the luminance adjustment unit 140 increases the luminance of the light emitting units 111.

Generally, the ripple-free component of the PPG pulse refers to the signal which is reflected from portions of the human body having regular volume, such as bones, skin pigments and the tissue of the human body, and is then measured therefrom, rather than signals attributable to variation in the volume of artery blood vessels. Therefore, the ripple-free component is information which is used by a pulse oximeter for calculating oxygen saturation, but is filtered out during a process for measuring a PPG pulse.

When the PPG pulse is measured, the influence of measurement components, for example, clothing, is included in the ripple-free component and has a certain value attributable to the clothing. When the PPG pulse can maintain a suitable magnitude of the ripple-free component using the above properties, the luminance of the light emitting units can be adjusted to a suitable level required to measure a PPG pulse through clothing.

The filter and amplification unit 150 includes a filter for eliminating noise from the ripple component and an amplifier for amplifying a filtered ripple component.

The A/D conversion unit 160 converts the output of the filter and amplification unit 150 into a digital signal.

The signal transmission unit 170 transmits the output of the A/D conversion unit 160 to an external device.

Hereinafter, a second embodiment of a non-contact PPG pulse measurement device according to the present invention will be described in detail.

As shown in FIG. 1, a non-contact PPG pulse measurement device according to a second embodiment of the present invention includes a sensing unit 110, a signal separation unit 120, a microprocessor unit 130, a luminance adjustment unit 140, a filter and amplification unit 150, an A/D conversion unit 160, and a signal transmission unit 170.

The sensing unit 110 is implemented using reflection-type sensors, and includes a light emitting unit for emitting light, and at least two light receiving units for sensing light which has been emitted from the light emitting unit and has been reflected from a human body.

The light emitting unit is implemented as a Light Emitting Diode (LED) which emits infrared light, and the light receiving units are implemented as photodetectors. In this case, a plurality of light receiving units may be arranged around and near the light emitting unit. That is, the light emitting unit may be arranged at the center of a circle having a predetermined radius, and the light receiving units may be arranged on the circumference of the circle.

As shown in FIGS. 3A and 3B, the sensing unit 110 includes three light receiving units 112 so that the light receiving units 112 are arranged and spaced apart from each other at equal 120° intervals around the light emitting unit 111.

The signal separation unit 120, the microprocessor unit 130, the luminance adjustment unit 140, the filter and amplification unit 150, the A/D conversion unit 160 and the signal transmission unit 170 according to the second embodiment are identical to those of the non-contact PPG pulse measurement device according to the first embodiment. Preferably, a value set in the microprocessor unit 130 may be 1V to 2V.

Hereinafter, a non-contact oxygen saturation measurement device according to a first embodiment of the present invention will be described in detail.

As shown in FIG. 1, a non-contact oxygen saturation measurement device according to an embodiment of the present invention includes a sensing unit 110, a signal separation unit 120, a microprocessor unit 130, a luminance adjustment unit 140, a filter and amplification unit 150, an A/D conversion unit 160 and a signal transmission unit 170.

The sensing unit 110 measures the oxygen saturation of a human body, but measures the oxygen saturation of a user without making direct contact with the user's skin in an unconstrained manner, that is, without the user's awareness of the measurement being taken.

The sensing unit 110 includes at least four light emitting units for emitting light having different wavelengths, and a light receiving unit arranged around the light emitting units and configured to sense light reflected from the human body, wherein the number of light emitting units that emit light having each wavelength is uniform.

As one possible embodiment, the sensing unit 110 may be configured such that four light emitting units are arranged on the circumference of a circle having a predetermined radius and the light receiving unit is arranged at the center of the circle. In this case, the light emitting units may include two light emitting units for emitting red light to correspond to two light emitting units for emitting infrared light. At this time, the two light emitting units for emitting the red light may be arranged and spaced apart from each other at equal 180° intervals around the light receiving unit.

Further, as another embodiment, as shown in FIG. 4A, the sensing unit 110 may be configured such that six light emitting units 111a and 111b are arranged on the circumference of a circle having a predetermined radius and the light receiving unit 112 is arranged at the center of the circle. In this case, three light emitting units 111b for emitting red light may be included in the sensing unit 110 to correspond to the three light emitting units 111a for emitting infrared light. At this time, the three light emitting units 111b for emitting the red light may be arranged and spaced apart from each other at equal 120° intervals around the light receiving unit 112.

Furthermore, the light emitting units 111a for emitting infrared light and the light emitting units 111b for emitting red light may be sequentially and alternately arranged so that they are arranged and spaced apart from each other at equal 60° intervals around the light receiving unit 112. Here, the distance between each of the light emitting units 111a and 111b and the center of the light receiving unit 112 may be 10 mm.

The signal separation unit 120 classifies the output of the sensing unit 110 into respective wavelengths so as to measure PPG pulses for respective wavelengths, and separates each output classified into respective wavelengths into a ripple component and a ripple-free component using a filter.

The microprocessor unit 130, the luminance adjustment unit 140, the filter and amplification unit 150, the A/D conversion unit 160 and the signal transmission unit 170 are identical to those of the non-contact PPG pulse measurement device according to the embodiment of the present invention.

Hereinafter, a non-contact oxygen saturation measurement device according to a second embodiment of the present invention will be described in detail.

As shown in FIG. 1, a non-contact oxygen saturation measurement device according to a second embodiment of the present invention includes a sensing unit 110, a signal separation unit 120, a microprocessor unit 130, a luminance adjustment unit 140, a filter and amplification unit 150, an A/D conversion unit 160, and a signal transmission unit 170.

The sensing unit 110 includes at least two light emitting units for emitting light having different wavelengths to a human body without making direct contact with the skin and at least two light receiving units arranged around the light emitting units and configured to sense light reflected from the human body, wherein the number of light emitting units that emit light having each wavelength is uniform.

The sensing unit 110 is configured such that two light emitting units are implemented and arranged in parallel around the center of a circle having a predetermined radius, as shown in FIG. 4B. In this case, the light emitting units include one light emitting unit 111b for emitting red light to correspond to one light emitting unit 111a for emitting infrared light. The light receiving units 112 may be arranged on the circumference of the circle. In this case, the light receiving units 112 may be implemented using three light receiving units so that they are arranged and spaced apart from each other at equal 120° intervals around the center of the circle on which the light receiving units 112 are arranged.

Meanwhile, it is apparent that the light emitting unit 111a for emitting infrared light and the light emitting unit 111b for emitting red light must emit light having the same intensity so that oxygen saturation can be measured.

The signal separation unit 120, the microprocessor unit 130, the luminance adjustment unit 140, the filter and amplification unit 150, the A/D conversion unit 160 and the signal transmission unit 170 are identical to those of the non-contact oxygen saturation measurement device according to the first embodiment of the present invention.

Generally, the term 'oxygen saturation' means the ratio of the density of oxygen hemoglobin to the density of total hemoglobin. The absorption factor of the infrared light increases when the infrared light passes through oxygen hemoglobin, and decreases when it passes through reduced hemoglobin. In contrast, the absorption factor of the red light decreases when the red light passes through oxygen hemoglobin, and increases when it passes through reduced hemoglobin. As described above, the infrared light is absorbed well by oxygen hemoglobin and the red light is absorbed well by reduced hemoglobin. Accordingly, the oxygen saturation can be measured using both the difference between the absorption factors of two wavelengths and the PPG pulse signals of the two wavelengths.

In order to measure the PPG pulses of respective wavelengths, a pulse oximeter, implemented using a demultiplexer (sample and hold circuit) for sequentially and alternately turning on the infrared light and the red light and separating an output signal in synchronization with the infrared light and the red light, may be employed.

Hereinafter, a non-contact blood pressure measurement device according to an embodiment of the present invention will be described in detail.

As shown in FIG. 8, a non-contact blood pressure measurement device according to an embodiment of the present invention includes a non-contact PPG pulse measurement device 100 according to the first or second embodiment of the present invention, a non-contact electrocardiogram measurement device 200, and a signal processing device 300.

The non-contact PPG pulse measurement device 100 is identical to that of the first or second embodiment of the present invention.

As shown in FIG. 5, the non-contact electrocardiogram measurement device 200 includes an amplifier-attached electrode 210, a filter and amplification unit 220, an A/D conversion unit 230, and a signal transmission unit 240.

The amplifier-attached electrode 210 includes at least one electrode, and measures an electrocardiogram in an unconstrained manner without making direct contact with the skin, that is, without the user's awareness of the measurement being taken. For example, the amplifier-attached electrode 210 comes into contact with the user's clothing in daily life while the user is wearing his or her clothes without being aware of the measurement being taken, thus enabling the electrocardiogram of a human body to be measured.

The filter and amplification unit 220 includes a filter for eliminating noise from a signal output from the amplifier-attached electrode 210 and an amplifier for amplifying a filtered signal.

The A/D conversion unit 230 converts the output of the filter and amplification unit 220 into a digital signal.

The signal transmission unit 240 transmits the output of the A/D conversion unit 230 to the signal processing device 300.

The signal processing device 300 includes a pulse arrival time calculation unit 310, a blood pressure information output unit 320, and a display unit 330.

The pulse arrival time calculation unit 310 calculates a pulse arrival time using both the signal transmitted from the non-contact PPG pulse measurement device 100 and the signal transmitted from the non-contact electrocardiogram measurement device 200.

Generally, as shown in FIG. 7, the term 'pulse arrival time' means a time interval from the R peak of the electrocardiogram to the characteristic point of the PPG pulse, in detail, the maximum point of the first derivative, that is, the steepest point. Since such a pulse arrival time is in inverse proportion to blood pressure, blood pressure can be estimated in real time.

The blood pressure information output unit 320 outputs blood pressure information corresponding to the pulse arrival time calculated by the pulse arrival time calculation unit 310 in conjunction with a blood pressure information Database (DB) in which pieces of blood pressure information corresponding to the pulse arrival times of the user are stored.

The display unit 330 displays the output of the blood pressure information output unit 320 on the screen.

Hereinafter, the operation of the non-contact PPG pulse measurement device according to the embodiment of the present invention, and the oxygen saturation measurement device and the blood pressure measurement device using the PPG pulse measurement device will be described.

A PPG pulse can be measured through the user's clothing without bringing the measurement device into direct contact with the skin of the user while the user is unaware of the measurement being taken. That is, the sensing unit of the non-contact PPG pulse measurement device according to the embodiment of the present invention is configured such that, in order to allow light to pass through the clothing and allow reflected light to also pass through the clothing and to be sensed, the light receiving unit 112 is arranged at the center of a circle having a predetermined radius and three light emitting units 111 are arranged and spaced apart from each other on the circumference of the circle at equal 120° intervals around the light receiving unit 112, as shown in FIGS. 2A and 2B.

The light emitted from the light emitting units 111 is radiated into a sensing area of the light receiving unit 112 by the human body, and the amount of radiated light is greater than that of light radiated into the sensing area of the conventional light receiving unit 20 of FIGS. 9A and 9B. Therefore, the sensing unit of the present invention can obtain a signal having higher output than the conventional sensing unit.

Further, as shown in FIGS. 3A and 3B, the sensing unit 110 is configured such that the light emitting unit 111 is arranged at the center of a circle having a predetermined radius, and three light receiving units 112 are arranged and spaced apart from each other on the circumference of the circle at equal 120° intervals. When the amounts of light sensed by the respective light receiving units 112 are summed up, a signal having higher output than that of the conventional sensing unit can be obtained.

As shown in FIG. 1, the output of the sensing unit 110 is separated into a ripple component and a ripple-free component by the signal separation unit 120. The ripple-free component is determined through comparison with a preset DC signal value by the monitoring of the microprocessor unit 130. Preferably, the DC signal value set in the microprocessor unit 130 is 1V to 2V.

Therefore, the luminance adjustment unit 140 decreases the luminance of the light emitting unit 111 in response to a control signal output from the microprocessor unit 130 when the value of the ripple-free component is greater than 2V, and increases the luminance when the value of the ripple-free component is less than 1V, thus measuring a suitable PPG pulse even through clothing without making direct contact with the skin.

Meanwhile, noise is eliminated from the ripple component separated by the signal separation unit 120 by the filter and amplification unit 150, and the noise-eliminated signal is amplified. The amplified signal is converted into a digital signal by the A/D conversion unit 160, and is then transmitted to an external device by the signal transmission unit 170.

The present invention enables oxygen saturation, as well as the above-described PPG pulse, to be measured on the clothing without making direct contact with the skin while the user is unaware of the measurement being taken.

The sensing unit of the non-contact oxygen saturation measurement device according to the embodiment of the present invention is configured to include light emitting units 111b, which are implemented as LEDs for emitting red light having the same intensity as that of infrared light, to correspond to light emitting units 111a for emitting the infrared light, as shown in FIGS. 4A and 4B. In this case, as shown in FIG. 4A, the light emitting units may be arranged on the circumference of a circle having a predetermined radius, and the light receiving unit 112 is arranged at the center of the circle. In this case, the sensing unit may include three light emitting units 111b for emitting red light to correspond to three light emitting units 111a for emitting infrared light. Further, since a pulse oximeter for measuring the PPG pulses of respective wavelengths may be configured, suitable oxygen saturation can be measured even on clothing without making direct contact with the skin by using both the difference between the absorption factors of the two wavelengths and the PPG pulses of the two wavelengths.

Further, the present invention can measure blood pressure without making direct contact with the skin by using the signals transmitted from the PPG pulse measurement device and the electrocardiogram measurement device.

That is, as shown in FIGS. 6A and 6B, the sensing unit 110 of the non-contact PPG pulse measurement device may be installed at a predetermined location on the top surface of a chair coming into contact with the user's hips and may measure the PPG pulse of an examinee (user) on a thigh portion of the user in an unconstrained manner. Further, at least one amplifier-attached electrode 210 of the non-contact electrocardiogram measurement device may be installed on both suitable sides of the back of the chair and measure the electrocardiogram of the examinee in an unconstrained manner.

As shown in FIG. 8, the measured values are transmitted to the signal processing device 300 through the respective signal transmission units 170 and 240. The pulse arrival time calculation unit 310 of the signal processing device 300 calculates the pulse arrival time using respective transmitted signals. The blood pressure information output unit 320, operating in conjunction with the blood pressure information DB, detects blood pressure information corresponding to the calculated pulse arrival time, and the display unit 330 displays the blood pressure information.

As described above, although the non-contact PPG pulse measurement device and the blood pressure measurement device using the PPG pulse measurement device according to the present invention have been described with reference to the attached drawings, it is apparent that the present invention is not limited by the embodiments and drawings disclosed in the present specification, and various modifications, additions and substitutions may be implemented by those skilled in the art, without departing from the scope and spirit of the invention as disclosed in the accompanying claims.

As described above, a non-contact PPG pulse measurement device according to the present invention is advantageous in that, since high-luminance light is emitted, the measurement device can measure the PPG pulse of a user in the state in which the user is wearing his or her clothes without making direct contact with the user's skin while the user is unaware of the measurement being taken.

Further, the present invention is advantageous in that, since the luminance of light can be adjusted, the measurement device can be applied to various types of clothing having different thicknesses, and the PPG of the user can be measured in an unconstrained manner using tools encountered by the user in his or her daily life, such as when sitting down on a chair or lying down on a bed.

Further, the present invention is advantageous in that, since light having different wavelengths can be emitted and the luminance of the light can be adjusted, the oxygen saturation of the user can be measured through the user's clothing in an unconstrained manner.

Further, the present invention is advantageous in that a pulse arrival time can be measured in conjunction with an electrocardiogram measurement system capable of performing measurement through clothing, thus enabling blood pressure to be continuously estimated.

Furthermore, the present invention is advantageous in that long-term health management is made possible by the continuous monitoring of a heart rate, heart rate variability, blood pressure and oxygen saturation, and a biofeedback effect can be realized through the measurement of multiple biological signals.

In addition, the present invention is advantageous in that remote health management is possible through the connection to a server over a communication network.

What is claimed is:

1. A non-contact blood pressure measurement device, comprising:
a non-contact photoplethysmographic (PPG) pulse measurement device;
a non-contact electrocardiogram measurement device for measuring an electrocardiogram without making direct contact with skin; and
a signal processing device for outputting blood pressure information using both a signal transmitted from the non-contact PPG pulse measurement device and a signal transmitted from the non-contact electrocardiogram measurement device,
wherein the non-contact photoplethysmographic (PPG) pulse measurement device comprises:
a sensing unit including at least two light emitting units for emitting light into a human body without the light emitting units making direct contact with skin of a user, and a light receiving unit configured to sense light reflected from the human body;
a signal separation unit implemented as a filter for separating an output of the sensing unit into a ripple component and a ripple-free component;
a microprocessor unit configured to monitor the ripple-free component, compare a value of the ripple-free component with a preset Direct Current (DC) signal value, and generate a control signal commanding luminance to be increased when the value of the ripple-free component is less than the preset Direct Current (DC) signal value and to be decreased when the value of the ripple-free component is greater than said preset Direct Current (DC) signal value;
a luminance adjustment unit configured to adjust luminance of the light emitting units in response to the control signal output from the microprocessor unit;
a filter and amplification unit including a filter for eliminating noise from the ripple component and an amplifier for amplifying a filtered ripple component;
an Analog/Digital (A/D) conversion unit configured to convert an output of the filter and amplification unit into a digital signal; and
a signal transmission unit configured to transmit an output of the A/D conversion unit to an external device, wherein said at least two light emitting units are arranged on a circumference of a circle having a predetermined radius and the light receiving unit is arranged at the center of the circle, and
wherein the non-contact electrocardiogram measurement device comprises:
an amplifier-attached electrode;
a filter and amplification unit including a filter for eliminating noise from a signal output from the amplifier-attached electrode, and an amplifier for amplifying a filtered signal;
an A/D conversion unit for converting an output of the filter and amplification unit into a digital signal; and
a signal transmission unit for transmitting an output of the A/D conversion unit to the signal processing device, wherein the amplifier-attached electrode of the non-contact electrocardiogram measurement device is installed on both suitable sides of the back of a chair to measure the electrocardiogram of a user in an unconstrained manner.

2. The non-contact blood pressure measurement device according to claim 1, wherein said at least two light emitting units include three light emitting units.

3. The non-contact blood pressure measurement device according to claim 2, wherein said three light emitting units are arranged on a circumference of a circle and spaced apart from each other at equal 120° intervals around the light receiving unit.

4. The non-contact blood pressure measurement device according to claim 1, wherein the signal processing device comprises:
a pulse arrival time calculation unit for calculating a pulse arrival time using the signals transmitted from the non-contact PPG pulse measurement device and the non-contact electrocardiogram measurement device;
a blood pressure information output unit for outputting blood pressure information corresponding to the pulse arrival time calculated by the pulse arrival time calculation unit in conjunction with a blood pressure information database; and a display unit for displaying an output of the blood pressure information output unit on a screen.

5. The non-contact blood pressure measurement device according to claim 1,
wherein the sensing unit of the non-contact PPG pulse measurement device is installed at a predetermined location on the top surface of a chair configured to contact a user's hips to measure the PPG pulse of the user on a thigh portion of the user in an unconstrained manner.

6. The non-contact blood pressure measurement device according to claim 1, wherein said at least two light emitting units include three light emitting units.

7. The non-contact blood pressure measurement device according to claim 1, wherein the preset Direct Current (DC) signal value preset in the microprocessor unit is 1V to 2V.

8. The non-contact blood pressure measurement device according to claim 1,
wherein the sensing unit of the non-contact PPG pulse measurement device is installed at a predetermined location on the top surface of a chair configured to come into contact with a user's hips to measure the PPG pulse of the user on a thigh portion of the user in an unconstrained manner.

9. The non-contact blood pressure measurement device according to claim 1, wherein said at least two light emitting units include three light emitting units.

10. The non-contact blood pressure measurement device according to claim 1, wherein the preset Direct Current (DC) signal value preset in the microprocessor unit is 1V to 2V.

11. A non-contact blood pressure measurement device, comprising:
a non-contact photoplethysmographic (PPG) pulse measurement device;
a non-contact electrocardiogram measurement device for measuring an electrocardiogram without making direct contact with skin; and
a signal processing device for outputting blood pressure information using both a signal transmitted from the non-contact PPG pulse measurement device and a signal transmitted from the non-contact electrocardiogram measurement device,
wherein the non-contact photoplethysmographic (PPG) pulse measurement device comprises:
a sensing unit including a light emitting unit for emitting light into a human body without the light emitting unit making direct contact with skin, and at least two light receiving units arranged around the light emitting unit and configured to sense light reflected from the human body;
a signal separation unit implemented as a filter for separating an output of the sensing unit into a ripple component and a ripple-free component;
a microprocessor unit configured to monitor the ripple-free component, compare a value of the ripple-free component with a preset Direct Current (DC) signal value, and generate a control signal commanding luminance to be increased when the value of the ripple-free component is less than the preset Direct Current (DC) signal value and to be decreased when the value of the ripple-free component is greater than said preset Direct Current (DC) signal value;
a luminance adjustment unit configured to adjust luminance of the light emitting units in response to the control signal output from the microprocessor unit;
a filter and amplification unit including a filter for eliminating noise from the ripple component and an amplifier for amplifying a filtered ripple component;
an Analog/Digital (A/D) conversion unit configured to convert an output of the filter and amplification unit into a digital signal; and
a signal transmission unit configured to transmit an output of the A/D conversion unit to an external device,
wherein the light emitting unit is arranged at a center of a circle having a predetermined radius, and said at least two light receiving units are arranged on a circumference of the circle, and
wherein the non-contact electrocardiogram measurement device comprises:
an amplifier-attached electrode;
a filter and amplification unit including a filter for eliminating noise from a signal output from the amplifier-attached electrode, and an amplifier for amplifying a filtered signal;
an A/D conversion unit for converting an output of the filter and amplification unit into a digital signal; and
a signal transmission unit for transmitting an output of the A/D conversion unit to the signal processing device, wherein the amplifier-attached electrode of the non-contact electrocardiogram measurement device is installed on both suitable sides of the back of a chair to measure the electrocardiogram of a user in an unconstrained manner.

12. The non-contact blood pressure measurement device according to claim 11, wherein said at least two light receiving units include three light receiving units.

13. The non-contact blood pressure measurement device according to claim 12, wherein said three light receiving units are arranged on a circumference of a circle and spaced apart from each other at equal 120° intervals around the light emitting unit.

14. The non-contact blood pressure measurement device according to claim 12, wherein said three light receiving units are arranged on a circumference of a circle and spaced apart from each other at equal 120° intervals around the light emitting unit.

15. The non-contact blood pressure measurement device according to claim 11, wherein the signal processing device comprises:
a pulse arrival time calculation unit for calculating a pulse arrival time using the signals transmitted from the non-contact PPG pulse measurement device and the non-contact electrocardiogram measurement device;
a blood pressure information output unit for outputting blood pressure information corresponding to the pulse arrival time calculated by the pulse arrival time calculation unit in conjunction with a blood pressure information database; and
a display unit for displaying an output of the blood pressure information output unit on a screen.

16. The non-contact blood pressure measurement device according to claim 11, wherein said three light emitting units are arranged on a circumference of a circle and spaced apart from each other at equal 120° intervals around the light receiving unit.

* * * * *